US012422422B2

(12) United States Patent
Mayer et al.

(10) Patent No.: US 12,422,422 B2
(45) Date of Patent: Sep. 23, 2025

(54) INTERNAL COMBUSTION ENGINE WITH A GENERATOR AND A CARBON MONOXIDE SENSOR

(71) Applicant: Andreas Stihl AG & Co. KG, Waiblingen (DE)

(72) Inventors: Felix Mayer, Waiblingen (DE); Manuel Dangelmaier, Wernau (DE)

(73) Assignee: Andreas Stihl AG & Co. KG, Waiblingen (DE)

( * ) Notice: Subject to any disclaimer, the term of this patent is extended or adjusted under 35 U.S.C. 154(b) by 0 days.

(21) Appl. No.: 18/503,224

(22) Filed: Nov. 7, 2023

(65) Prior Publication Data

US 2024/0151698 A1  May 9, 2024

(30) Foreign Application Priority Data

Nov. 9, 2022 (DE) ......................... 102022129665.2

(51) Int. Cl.
 *G01N 33/00* (2006.01)
 *F02B 63/04* (2006.01)

(52) U.S. Cl.
 CPC ....... *G01N 33/0027* (2013.01); *F02B 63/042* (2013.01); *F02B 63/044* (2013.01)

(58) Field of Classification Search
 CPC .. F02B 63/042; F02B 63/044; G01N 33/0027
 USPC ...................................................... 73/23.31
 See application file for complete search history.

(56) References Cited

U.S. PATENT DOCUMENTS

| 4,033,122 A | 7/1977 | Masaki et al. |
| 10,697,340 B1 | 6/2020 | Joo et al. |
| 2012/0282561 A1* | 11/2012 | Kaiser ............... F24H 1/0027 432/92 |
| 2015/0077243 A1* | 3/2015 | Hooper ............... G08B 17/06 340/532 |

FOREIGN PATENT DOCUMENTS

| DE | 2452503 A1 | 9/1975 |
| DE | 102018203491 A1 | 9/2019 |
| DE | 102019120946 A1 | 12/2019 |
| DE | 102019208436 A1 | 8/2020 |
| DE | 102020004416 A1 | 10/2020 |

* cited by examiner

*Primary Examiner* — Lindsay M Low
*Assistant Examiner* — Omar Morales
(74) *Attorney, Agent, or Firm* — Smartpat PLC

(57) ABSTRACT

A generator provides a supply voltage for an electrical consumer. It includes an internal combustion engine driving the generator. An electrical control unit has an incoming electrical line for supplying an operating voltage thereto. The control unit further has at least one outgoing electrical line. The outgoing electrical line is connected to at least one operating unit that is necessary for operating the internal combustion engine. In order to switch off the internal combustion engine in the event of an increased CO concentration in the vicinity of the generator, a breaker is arranged in an electrical line of the control unit. The breaker is controlled by a CO sensor, which is designed to open the breaker and interrupt the electrical line when a predeterminable CO limit value is exceeded.

12 Claims, 3 Drawing Sheets

INTERNAL COMBUSTION ENGINE WITH A GENERATOR AND A CARBON MONOXIDE SENSOR

CROSS-REFERENCE TO RELATED APPLICATION

This application claims the benefit of German Patent Application DE 102022129665.2, filed on Nov. 9, 2022, the contents of which is incorporated in its entirety.

SUMMARY

The disclosure relates to a generator for providing a supply voltage for an electrical consumer. The generator is powered by an internal combustion engine. To operate the internal combustion engine, fuel is supplied thereto via a device. The fuel is ignited and burned by a spark plug in the combustion chamber of the internal combustion engine. A crankshaft is driven to rotate by an ascending and descending piston.

The internal combustion engine is operated via an electrical control unit, which is connected to an incoming electrical line for supplying an operating voltage. When the operating voltage is applied, the control unit controls operating units of the internal combustion engine. The control unit has one or more outgoing electrical lines via which operating units that are necessary for operating the internal combustion engine, such as a spark plug, a fuel valve or the like, are connected.

The control unit of the internal combustion engine comprises a large number of electronic components, the interaction of which is coordinated with great effort. The internal combustion engine, the generator and a protective device against excessive CO concentrations should form a unit that can be operated robustly and reliably.

The invention is based on the object of specifying a robust system comprising an internal combustion engine, a generator, and a protective device which ensures a safe shutdown of the internal combustion engine in the vicinity of the generator and/or the internal combustion engine without intervention in the control unit itself.

The task is solved in a simple manner in that a breaker, which is controlled by a CO sensor, is arranged in an electrical line of the control unit in an internal combustion engine driving a generator. The breaker is controlled via a CO sensor in such a way that when a predeterminable CO limit value is exceeded, the breaker is opened to interrupt the electrical line.

In a simple embodiment of the invention, the breaker is arranged in the electrical line supplying the operating voltage to the control unit, which can also be referred to as the incoming electrical line. If the internal combustion engine is in operation and the CO sensor responds, the breaker opens, and the control unit is de-energized. It is not possible to operate the internal combustion engine with a de-energized control unit. The internal combustion engine is switched off without any intervention in the control unit itself.

In a further embodiment of the invention, the breaker can be arranged in an outgoing electrical line from the control unit to an operating unit of the internal combustion engine, the operating unit being necessary for operating the internal combustion engine. For example, the operating unit can be a spark plug that projects into the combustion chamber of the internal combustion engine. The breaker may then interrupt (open) an electrical line between the spark plug and an ignition unit. This means that no further spark can occur at the spark plug; the internal combustion engine stops.

The operating unit can also be an ignition unit connected to the spark plug, which, for example, generates the high voltage to trigger an ignition spark. If the ignition unit itself is de-energized by the breaker, the high voltage can no longer be generated. No spark can occur at the spark plug. The internal combustion engine stops.

In a further embodiment of the invention, the operating unit necessary for operating the internal combustion engine can be a device for supplying fuel. An electromagnetic fuel valve can be arranged in the device for supplying fuel. If the electrical line branch of the control unit leading to the fuel valve is opened by a breaker arranged therein, the fuel valve remains without function and the internal combustion engine stops.

A device for supplying fuel is understood to refer to a supply of fuel into a mixture forming device of the intake duct, into the intake manifold or also a direct injection into the combustion chamber.

The electromagnetic fuel valve is in particular a normally closed fuel valve, which requires an operating voltage or an operating pulse to open. If an outgoing electrical line branch of the control unit leading to the fuel valve is opened by a breaker arranged therein, the power supply to the fuel valve is interrupted. The fuel valve remains closed. No further fuel is supplied to the internal combustion engine. The internal combustion engine stops.

The CO sensor is connected to a control module. The control module is provided and designed to evaluate the output signal of the CO sensor. The control module compares the output signal of the CO sensor with a predetermined limit value. If the predetermined CO limit value is exceeded, the control module activates the breaker and opens it. The line branch in which the breaker is arranged is interrupted.

The CO sensor, the breaker, and the control module are advantageously arranged in a common housing. The structural unit formed in this way can be mounted and electrically connected at a suitable location on the generator with a high degree of flexibility in the arrangement.

The breaker is advantageously a normally open breaker. The breaker will be closed if and only if the control module is supplied with an operating voltage. If there is an operating voltage at the control module, the breaker is closed. If the control module's operating voltage fails, the breaker opens.

The breaker is preferably an electromechanical switch that inevitably opens if the operating voltage fails. A semiconductor element may be used as a breaker.

The housing with the CO sensor, the breaker arranged therein, and the control module for actuating the breaker form an independent structural unit with an electrical input and an electrical output. This enables a retrofit installation in a generator that is driven by an internal combustion engine, whereby one line branch only has to be separated and the cable ends connected to the corresponding connections of the independent structural unit. A simple, practical arrangement is the arrangement in the line branch of the operating voltage to the control unit.

The features disclosed in the claims, the description and the drawings can be combined with one another, regardless of the exemplary embodiment for which the features are specified. A combination of features from different exemplary embodiments is also possible.

DETAILED DESCRIPTION

Figure 1:
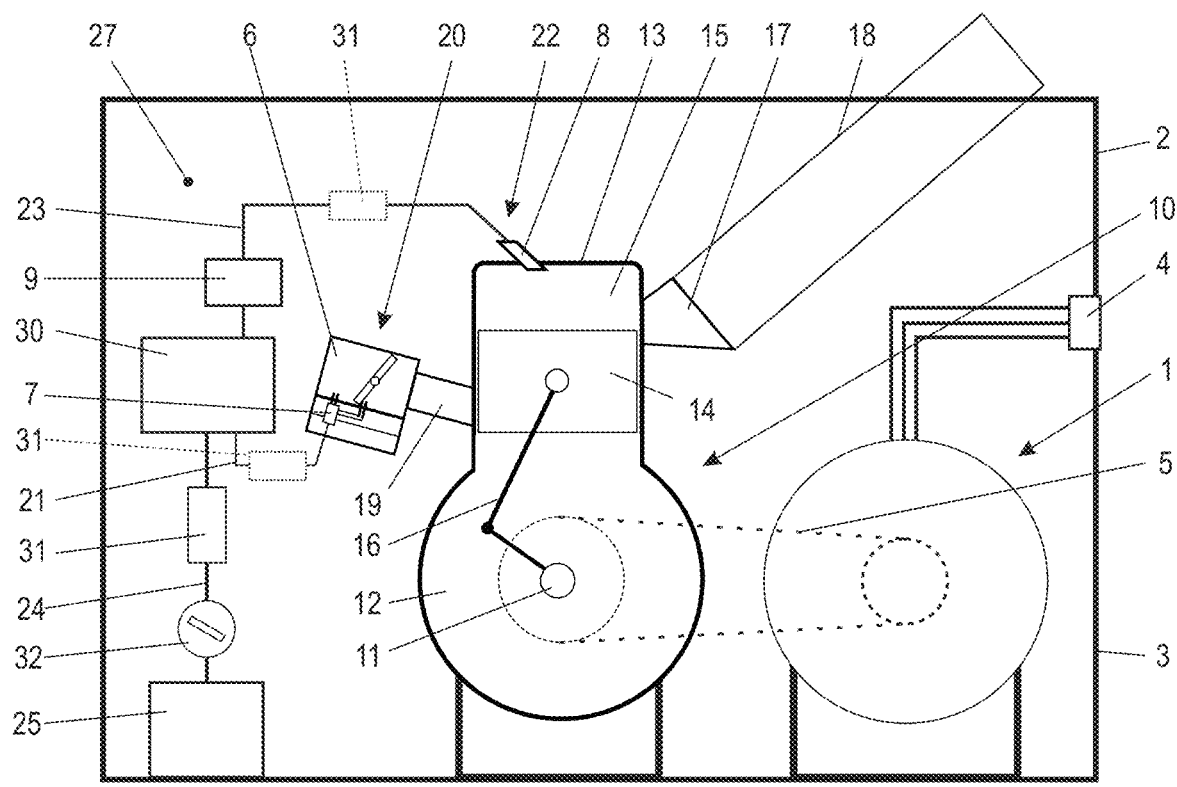
FIG. 1 is a schematic representation of a generator driven by an internal combustion engine.

FIG. 1 schematically shows a generator 1, which is driven by an internal combustion engine 10. In the schematic representation, the internal combustion engine 10 drives the generator 1 via a drive connection 5, for example via a belt drive or the like. Other arrangements may be used, in particular the generator 1 may be directly connected to a crankshaft 11 of the internal combustion engine 10 by a flange.

In the schematic representation, the internal combustion engine 10 and the generator 1 are arranged in a common housing 2. The housing can be an insulated housing to reduce operating noise. A voltage connection 4 for tapping the generator voltage is provided in a housing wall 3.

The internal combustion engine 10 has a crankcase 12 with the crankshaft 11 rotatably mounted therein. A piston 14 is arranged in a cylinder 13 of the internal combustion engine 10 and, together with the cylinder 13, delimits the combustion chamber 15 of the internal combustion engine 10. The rising and falling piston 14 drives the crankshaft 11 in rotation via a connecting rod 16. The combustion gases are discharged from the combustion chamber 15 via an outlet 17 and discharged from the housing 2 via an exhaust pipe 18.

To operate the internal combustion engine 10, a fuel/air mixture is supplied to it, for example, via an inlet 19. The fuel/air mixture is formed in a device 6, which in the exemplary embodiment shown is designed as a carburetor, in particular as a membrane carburetor. Fuel is fed into the carburetor via an electromagnetic fuel valve 7. The fuel valve 7 is preferably normally closed. The device 6 for supplying a fuel/air mixture into the combustion chamber 15 of the internal combustion engine 10 forms an operating unit 20 that is necessary for operating the internal combustion engine.

Alternatively, to supply fuel to the internal combustion engine, the carburetor can also be designed as a float carburetor, or the fuel can be supplied to the internal combustion engine via an injection system without a carburetor.

The fuel valve 7 is controlled by a control unit 30. The control unit 30 is connected to the fuel valve 7 via an outgoing electrical line 21 extending from the control unit 30.

The control unit 30 is connected via a further outgoing electrical line 23 to a further operating unit 22 that is necessary for operating the internal combustion engine 10. The further operating unit 22 is formed by a spark plug 8, which is connected to the control unit 30 via an ignition unit 9.

In the illustrated embodiment showing the generator 1 being driven by an internal combustion engine 10, the control unit 30 is supplied with an operating voltage from an energy source 25. The energy source 25 can be a battery, a rechargeable battery or similar energy source 25.

The energy source 25 is connected to the control unit 30 via an electrical line 24. The electrical line 24 forms an incoming electrical line 24 leading to the control unit 30 for supplying the operating voltage.

A structural unit 31 is inserted into the incoming electrical line 24. A key switch 32 is provided electrically in series with the structural unit 31 in the line branch 24.

Figure 2:
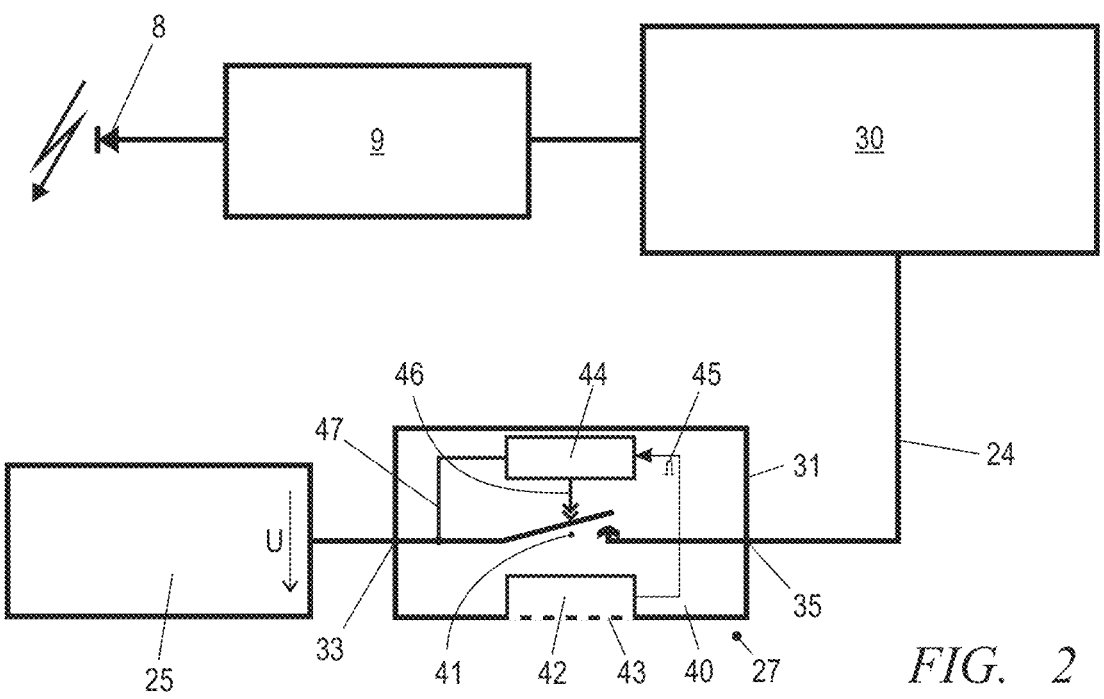
FIG. 2 is a block diagram showing a control unit for an internal combustion engine.

The structural unit 31 can be provided in the incoming electrical line 24 of the control unit 30 or in at least one further outgoing electrical line 21 or 23 of the control unit 30. The structural unit 31 is shown in detail in FIG. 2.

The structural unit 31 has a housing 40 in which a breaker 41 is arranged. The housing 40 has an electrical input 33 for connection to the breaker 41. The housing 40 also has an electrical output 35 which is connected to an outgoing connection of the breaker 41. The breaker 41 establishes an electrical connection between the input 33 and the output 35 or interrupts this electrical connection. The breaker 41 is a normally open breaker, preferably an electromechanical switch such as a relay or the like.

A CO sensor 42 is also provided in the housing 40, which exchanges air with the environment 27 via a suitably designed opening 43. The CO sensor 42 measures the carbon monoxide content in the ambient air. The output of the CO sensor is connected to a control module 44. The control module 44 evaluates the supplied output signal 45 of the CO sensor 42. It compares the output signal 45 with a predetermined limit value that is preferably stored in the control module 44. If the carbon monoxide content exceeds the predetermined limit value, the control module 44 opens the breaker 41. The electrical connection between the input 33 and the output 35 of the structural unit 31 is interrupted.

The operating voltage for the control module 44 is advantageously tapped directly at the input 33 of the structural unit 31 via a line 47.

The breaker 41 is a normally open breaker. That is, if there is no operating voltage U at the input 33 of the structural unit 31, the control module 44 is de-energized and cannot close the breaker 41. The breaker 41 remains in its open idle state. If the electrical supply line from the energy source 25 is closed, for example by turning the key switch 32, the operating voltage U is applied to the structural unit 31. By tapping the voltage via the line 47, the operating voltage is also applied to the control module 44. The control module 44 becomes active and closes the breaker 41. The electrical connection of the control unit 30 to the energy source 25 is established. The operating voltage U is present at the control unit 30. The control unit 30 is ready for operation and can trigger an ignition spark on the spark plug 8 via the ignition unit 9. The internal combustion engine is in operation.

During operation of the internal combustion engine 10, the CO sensor 42 determines the CO content in the ambient air continuously or at predeterminable time intervals. The CO sensor 42 transmits the measured values of the CO content as an output signal 45 to the control module 44. The control module 44 compares the output signal 45 of the CO sensor 42 continuously or at predeterminable time intervals with a predetermined limit value. If the output signal 45 of the CO sensor 42 is above the predetermined limit value, the control module 44 opens the breaker 41 via a suitable operative connection 46.

When the breaker 41 is opened, the operating voltage U applied to the control unit 30 is switched off. The control unit 30 becomes de-energized and can no longer control the operation of the internal combustion engine 10. The internal combustion engine 10 stops.

Figure 3:
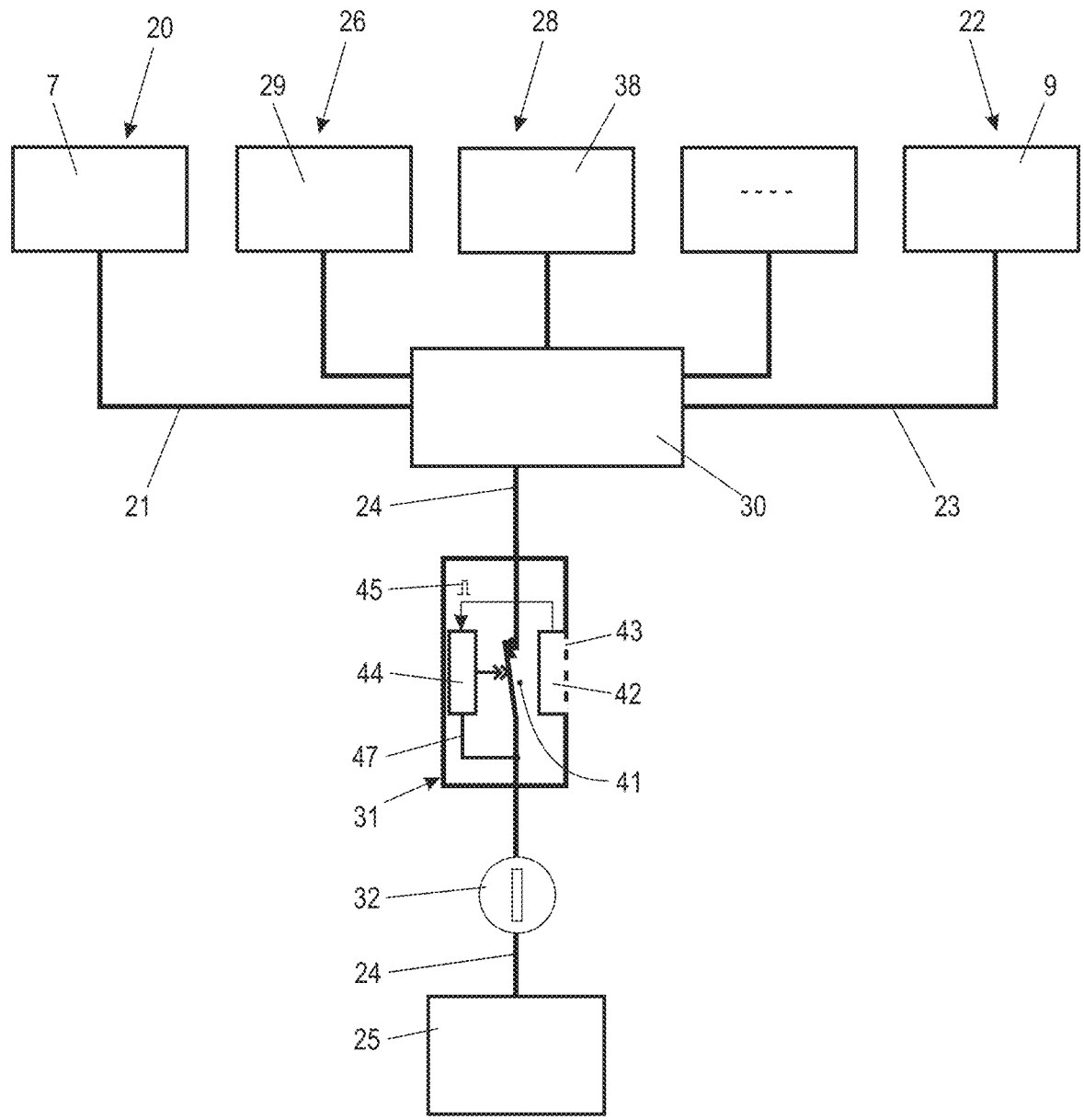
FIG. 3 shows a schematic representation of the control unit of an internal combustion engine with a breaker arranged in a line branch carrying the operating voltage.

In FIG. 3, the control unit 30 is shown with several operating units 20, 22, 26, 28 necessary for operating the internal combustion engine 10. The ignition unit 9 is shown as an exemplary operating unit 22. Another operating unit 20 necessary for operating the internal combustion engine 10 is provided by the fuel valve 7 in the device for mixture formation. Another operating unit 26 could be a gasoline pump 29 that feeds the fuel valve 7. A lambda sensor 38 provided in the system of the internal combustion engine 10 can also be understood as an operating unit 28. When the breaker 41 electrically disconnects the lambda sensor 38, the control unit 30 runs into an error and switches off the internal combustion engine 10. All of these operating units are dependent on the control unit 30 and cannot work without signals from the control unit 30 or, vice versa, the control unit 30 cannot operate without an input from the operating unit. Further operating units for switching off the internal combustion engine 10 are possible.

In FIG. 3 the key switch 32 is shown in the "ON" position, in which it switches the operating voltage of the energy source 25 to the breaker 41. The control module 44 takes its operating voltage from line 24 via line 47 and—as shown—closes the breaker 41. As a result, the operating voltage is also present at the control unit 30.

If, as shown in FIG. 3, the structural unit 31 with the CO sensor 42 and the breaker 41 is arranged in the electrical line 24 supplying the operating voltage to the control unit 30, opening the breaker 41 leads to a power failure on the control unit 30 with the result that all structural units 20, 22, 26, 28 no longer receive control signals and are passive. Without the operating units 20, 22, 26 and 28, operation of the internal combustion engine 10 is not possible; the internal combustion engine 10 stops.

Figure 4:
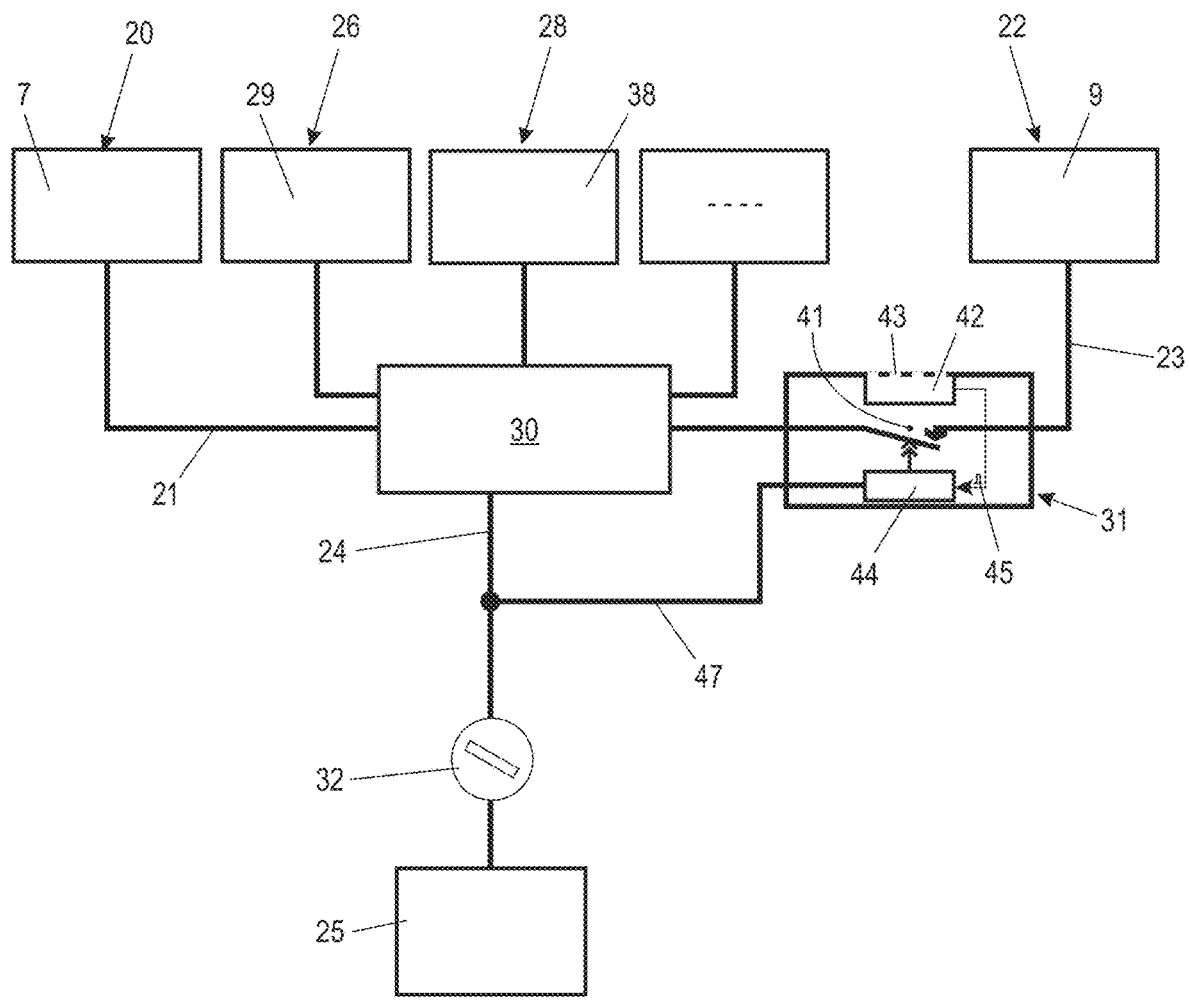
FIG. 4 is a schematic representation of the control unit of an internal combustion engine with a breaker arranged in an outgoing line branch to an operating unit of the internal combustion engine.

FIG. 3 shows the system for switching off an internal combustion engine 10 by deactivating all operating units 20, 22, 26, 28. It may be sufficient to switch off only one operating unit that is necessary to operate the internal combustion engine. This is shown in FIG. 4. The basic structure of the system in FIG. 4 for controlling an internal combustion engine 10 corresponds to that in FIG. 3. The same reference numbers are used for the same parts.

The structural unit 31 with the control module 44, the sensor 42 and the breaker 41 is provided in FIG. 4 in an outgoing electrical line 23 extending from the control unit 30. In the exemplary embodiment according to FIG. 4, the structural unit 31 is located in the outgoing electrical line 23 (also referred to as a control line) between the control unit 30 and the ignition module 9. Here, the ignition module 9 forms the operating unit 22 necessary for operating the internal combustion engine.

By turning the key switch, the operating voltage of the energy source 25 is applied to the control unit 30. A line 47 for supplying power to the control module 44 branches off between the key switch 32 and the control unit 30. As soon as the key switch 32 is set to "ON," the operating voltage will be simultaneously applied to the control module 44 and to the control unit 30. When voltage is applied to the control module 44, the breaker 41 is closed and the electrical line 23 between the ignition unit 9 and the control unit 30 is closed. The ignition unit 9 is ready for operation. The internal combustion engine 10 can start operating.

The CO sensor 42 detects the CO concentration of the environment 27 and reports this to the control module 44 as an output signal 45. The control module 44 compares the output signal 45 of the CO sensor 42 with a predetermined limit value. If the output signal 45 exceeds the limit value of a CO concentration, preferably stored in the control module 44, the breaker 41 is opened. The ignition unit 9 is no longer controlled by the control unit 30. The ignition of the internal combustion engine 10 fails. The internal combustion engine stops. The CO source has dried up.

The exemplary embodiments shown in FIGS. 3 and 4 can also be combined with one another. This results in a redundant system for switching off the internal combustion engine 10.

The breaker 41, which is switched depending on a CO sensor 42, can be arranged both in the voltage supply, i.e., in the supplying electrical line 24 of the control unit 30 and/or in one or more outgoing electrical lines 21 and 23 of the control unit 30, as shown schematically in FIG. 1.

What is claimed is:

1. A system for providing a supply voltage for an electrical consumer, comprising:
   a generator (1);
   an internal combustion engine (10) driving the generator (1);
   an electrical control unit (30) configured to control the internal combustion engine (10);
   an incoming electrical line (24) for supplying an operating voltage (U) to the electrical control unit (30);
   an operating unit (20, 22) that is necessary for operating the internal combustion engine (10);
   an outgoing electrical line (21, 23) connecting the electrical control unit (30) to the operating unit (20, 22);
   a breaker (41) arranged in the incoming electrical line (24) or the outgoing electrical line (21, 23); and
   a CO sensor (42) that controls the breaker (41),
   wherein the CO sensor (42) is configured to open the breaker (41) and interrupt the incoming electrical line (24) or the outgoing electrical line (21, 23) when a predeterminable CO limit value is exceeded and thereby shut down the internal combustion engine (10), and
   wherein the electrical control unit (30) is configured to control the internal combustion engine (10) by controlling the operating unit (20, 22) via the outgoing electrical line (21, 23).

2. The system according to claim 1,
   wherein the breaker (41) is arranged in the incoming electrical line (24) to the electrical control unit (30).

3. The system according to claim 1,
   wherein the breaker (41) is arranged in the outgoing electrical line (21, 23) to the operating unit (20, 22).

4. The system according to claim 1,
   wherein the operating unit (22) is a spark plug (8) which projects into a combustion chamber (15) of the internal combustion engine (10).

5. The system according to claim 4,
   wherein the operating unit (22) is an ignition unit (9) connected to the spark plug (8).

6. The system according to claim 1, further comprising:
   a device (6) for supplying fuel to operate the internal combustion engine (10),
   wherein the operating unit (20) is an electromagnetic fuel valve (7) arranged in the device (6).

7. The system according to claim 6,
   wherein the electromagnetic fuel valve is a normally closed fuel valve (7).

8. The system according to claim 1,
   wherein the CO sensor (42) is connected to a control module (44), and
   wherein the control module (44) is designed to evaluate an output signal (45) of the CO sensor (42), and wherein the control module (44) is configured to open the breaker (41) if the predeterminable CO limit value is exceeded.

9. The system according to claim 8,
wherein the CO sensor (42), the breaker (41), and the control module (44) are arranged in a common housing (40).

10. The system according to claim 9,
wherein the common housing (40) with the CO sensor (42), the breaker (41), and the control module (44) form an independent structural unit (31) with an electrical input (33) and an electrical output (35).

11. The system according to claim 1,
wherein the breaker (41) is a normally open breaker.

12. The system according to claim 1,
wherein the breaker (41) is an electromechanical switch.

\* \* \* \* \*